(12) United States Patent
Isoya et al.

(10) Patent No.: US 10,401,314 B2
(45) Date of Patent: Sep. 3, 2019

(54) HUMIDITY MEASURING DEVICE

(71) Applicant: Hitachi Automotive Systems, Ltd., Hitachinaka-shi, Ibaraki (JP)

(72) Inventors: Yuki Isoya, Hitachinaka (JP); Hiroaki Hoshika, Hitachinaka (JP); Takayuki Yogo, Hitachinaka (JP); Takahiro Miki, Hitachinaka (JP); Takahiro Yamamoto, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 184 days.

(21) Appl. No.: 15/539,799

(22) PCT Filed: Jan. 4, 2016

(86) PCT No.: PCT/JP2016/050003
§ 371 (c)(1),
(2) Date: Jun. 26, 2017

(87) PCT Pub. No.: WO2016/111253
PCT Pub. Date: Jul. 14, 2016

(65) Prior Publication Data
US 2017/0370862 A1 Dec. 28, 2017

(30) Foreign Application Priority Data
Jan. 8, 2015 (JP) .................. 2015-002430

(51) Int. Cl.
*G01N 33/00* (2006.01)
*G01N 25/64* (2006.01)
(Continued)

(52) U.S. Cl.
CPC ........... *G01N 25/64* (2013.01); *F02D 41/144* (2013.01); *F02D 41/1494* (2013.01);
(Continued)

(58) Field of Classification Search
CPC .... G01N 25/64; G01N 33/007; G01N 27/121; G01N 27/223; G01N 27/605;
(Continued)

(56) References Cited

U.S. PATENT DOCUMENTS 5,511,417 A 4/1996 Paukkunen
5,644,080 A 7/1997 Stormbom et al.
(Continued)

FOREIGN PATENT DOCUMENTS

DE 10 2010 030 338 A1 12/2011
JP 7-174721 A 7/1995
(Continued)

OTHER PUBLICATIONS

Extended European Search Report issued in counterpart European Application No. 16734992.7 dated Oct. 23, 2018 (five (5) pages).
(Continued)

*Primary Examiner* — Blake A Tankersley
(74) *Attorney, Agent, or Firm* — Crowell & Moring LLP

(57) ABSTRACT

The present invention obtains a humidity measuring device capable of performing self-diagnosis with high reliability. This humidity measuring device 20 has a diagnosis processing unit 25 for performing self-diagnosis by using gas temperatures and gas humidities before and after a gas in an ambient atmosphere to be measured is heat-controlled. The diagnosis processing unit has a diagnosis start determining unit 26 for determining whether the self-diagnosis can be started on the basis of an exchange state in the ambient atmosphere to be measured and the gas temperature and the gas humidity before the gas in the ambient atmosphere to be measured is heat-controlled, and a diagnosis continuation determining unit 28 for determining whether the self-diag-
(Continued)

nosis can be continued on the basis of the gas temperature and the gas humidity that are heat-controlled during the self-diagnosis.

8 Claims, 12 Drawing Sheets

(51) Int. Cl.
*F02M 35/10* (2006.01)
*F02D 41/14* (2006.01)
*F02D 41/22* (2006.01)
*F02D 41/24* (2006.01)
*F02D 41/28* (2006.01)
*F02D 41/04* (2006.01)

(52) U.S. Cl.
CPC ....... *F02D 41/222* (2013.01); *F02D 41/2438* (2013.01); *F02D 41/2448* (2013.01); *F02D 41/2474* (2013.01); *F02M 35/10393* (2013.01); *F02D 41/042* (2013.01); *F02D 41/28* (2013.01); *F02D 2041/285* (2013.01); *F02D 2200/0402* (2013.01); *F02D 2200/0414* (2013.01); *F02D 2200/0418* (2013.01); *Y02T 10/40* (2013.01)

(58) Field of Classification Search
CPC .. F02D 41/144; F02D 41/1494; F02D 41/222; F02D 41/2438; F02D 41/2448; F02D 41/2474; F02D 41/042; F02D 41/28; F02D 41/1479; F02D 41/146; F02D 41/2414; F02D 41/0065; F02D 2041/285; F02D 2200/0402; F02D 2200/0414; F02D 2200/0418; F02M 35/10393; F01N 3/0878; F01N 3/2053; F01N 2560/028
See application file for complete search history.

(56) References Cited

U.S. PATENT DOCUMENTS

| | | | |
|---|---|---|---|
| 2003/0089100 A1* | 5/2003 | Ueno | B01D 53/0454 60/277 |
| 2003/0106304 A1* | 6/2003 | Miyahara | F02D 41/222 60/277 |
| 2009/0044593 A1 | 2/2009 | Stormbom et al. | |
| 2013/0174644 A1 | 7/2013 | Schneider et al. | |
| 2014/0298880 A1 | 10/2014 | Pursifull et al. | |
| 2014/0316676 A1 | 10/2014 | Pursifull et al. | |
| 2015/0114087 A1* | 4/2015 | Sugiyama | G01M 15/102 73/28.01 |

FOREIGN PATENT DOCUMENTS

| | | |
|---|---|---|
| JP | 7-294469 A | 11/1995 |
| JP | 8-254579 A | 10/1996 |
| JP | 2002-156348 A | 5/2002 |
| JP | 2003-185614 A | 7/2003 |
| JP | 2008-541118 A | 11/2008 |
| JP | 2010-8323 A | 1/2010 |
| JP | 2010-237128 A | 10/2010 |
| JP | 2010-237130 A | 10/2010 |
| JP | 2013-529776 A | 7/2013 |

OTHER PUBLICATIONS

International Search Report (PCT/ISA/210) issued in PCT Application No. PCT/JP2016/050003 dated Mar. 29, 2016 with English-language translation (four (4) pages).

Japanese-language Written Opinion (PCT/ISA/237) issued in PCT Application No. PCT/JP2016/050003 dated Mar. 29, 2016 (five (5) pages).

* cited by examiner

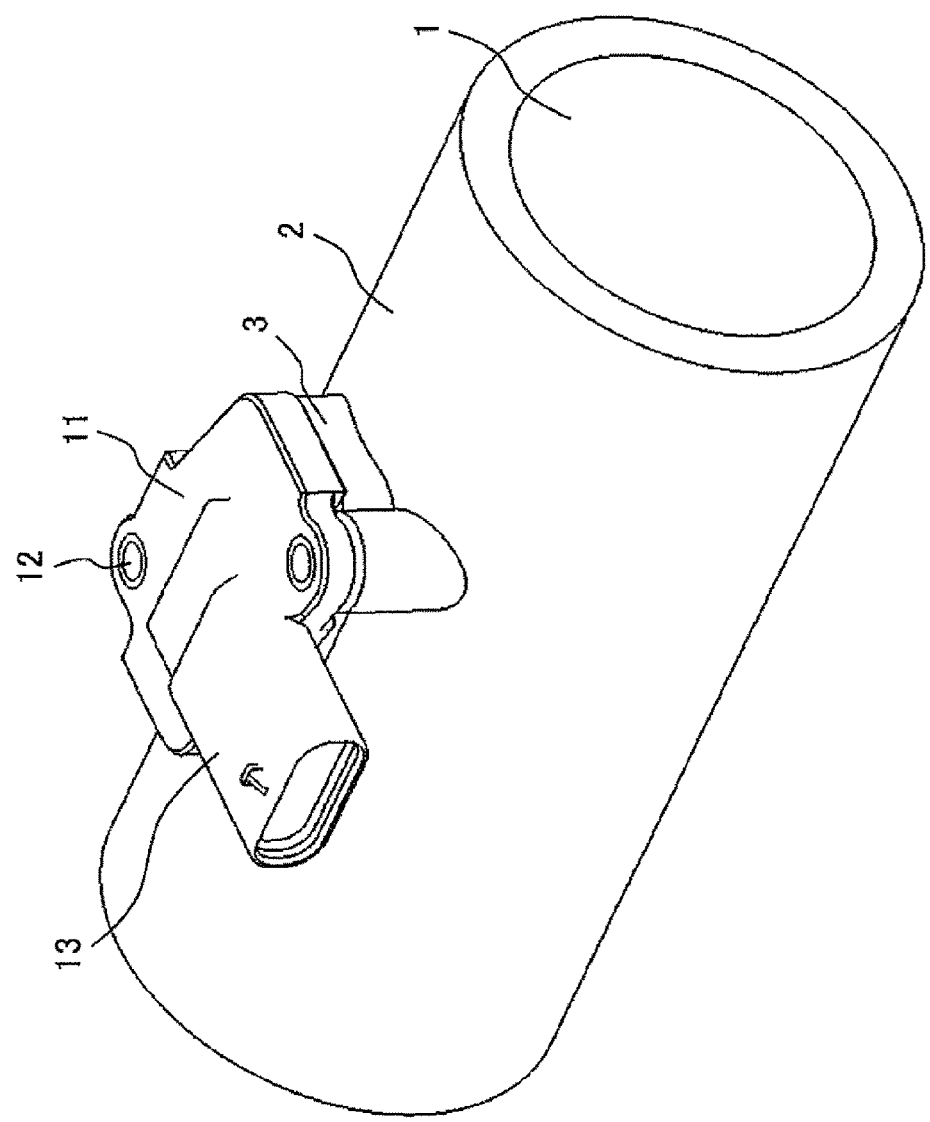

HUMIDITY MEASURING DEVICE

TECHNICAL FIELD

The present invention relates to a humidity measurement device, for example, that is attached to an intake system of an internal combustion engine of an automobile.

BACKGROUND ART

A humidity measurement device is one of the sensors that are attached to intake systems of internal combustion engines of automobiles for improved fuel economy and improved environmental performance. The humidity measurement device includes a measurement element of relative humidity, a measurement element of temperature provided near the measurement element of relative humidity, a heating element provided near the measurement element of relative humidity, and a circuit part that controls the measurement element of relative humidity, the measurement element of temperature, and the heating element. The humidity measurement device uses outputs of the measurement element of relative humidity and the measurement element of temperature, to calculate a specific humidity and externally transmits a signal corresponding to the specific humidity.

Here, there is a problem that gas to be measured flowing in an air intake system contains contaminants, such as dust, which could not be trapped by an air cleaner. The contaminants adhere to the measurement element of relative humidity, which degrades a measurement accuracy of relative humidity and accordingly degrades a calculation accuracy of a specific humidity in the humidity measurement device. PTL 1 is a conventional technique for recovering from the accuracy-degraded state caused by adhesion of contaminants to the measurement element of relative humidity.

PTL 1 discloses a technique that determines, under an environment that is not humidified or dehumidified, without a pressure change, a difference between dew-point temperatures of before heating and of during the heating, to self-diagnose whether a deterioration occurs to a degree requiring cleaning.

According to PTL 1, a degradation-diagnosis processing may be started in response to a starting instruction from a user, and may be started on a regular basis, and when the self-diagnosis determines that a humidity element is deteriorated, heating cleaning is performed to remove a component, in an atmosphere, that causes the deterioration of the humidity element, so that the humidity element can be recovered from the deterioration.

CITATION LIST

Patent Literature

PTL 1: JP 2010-237130 A

SUMMARY OF INVENTION

Technical Problem

However, the humidity measurement device that is attached to an intake system of an internal combustion engine of an automobile tends to cause a high temperature of the humidity measurement device itself, due to an influence of heat generated by the internal combustion engine. Therefore, when the measurement element of relative humidity is heated for a purpose of a diagnosis in such a high-temperature state, a self-destruction of the measurement element of relative humidity may occur.

Additionally, while a relative humidity is lowered because a saturated vapor amount is increased under a high temperature environment, in this condition, even when the measurement element of relative humidity is heated, a change in the relative humidity is small, and a significant difference required for a diagnosis, between states of before the heating and of during the heating, cannot be generated, which may degrade the accuracy.

Thus, it is preferable to define a temperature condition and a relative-humidity condition that allow the diagnosis, as well as an environmental condition where a specific humidity as a reference for the diagnosis is not changed. Further, it is clear that a diagnosis result is invalid when an unexpected diagnosis is performed, such as due to a change in the specific humidity as a reference itself, thus it is preferable to provide a safety measure, such as interposing an intermediate state between a steady state and a diagnostic state so as not to degrade a measurement accuracy of a measured value of temperature and a measured value of relative humidity during the diagnosis.

Furthermore, during the diagnosis, while the heating causes a change in temperature and a change in relative humidity, it is necessary to discriminate whether the changes are changes caused by the diagnosis, changes of an environment, or a failure of the measurement element of temperature or the measurement element of relative humidity. Therefore, it is preferable to send a control state of a heater element to a controller.

According to PTL 1, a self-diagnosis is performed under an environment that is not humidified or dehumidified, without a pressure change, and there is no communication measure for a condition of the heater element, or safety measure during a diagnosis process. Therefore, PTL 1 still has room to be improved for the above-mentioned problems.

The present invention has been made in consideration of the above-described problems, and it is an object of the invention to provide a humidity measurement device that is capable of a highly reliable self-diagnosis.

Solution to Problem

To achieve the above object, a humidity measurement device according to the present invention includes a processor of diagnosis for performing a self-diagnosis by using a gas temperature and a gas humidity before heating control of circumstances gas, and a gas temperature and a gas humidity that have been heating-controlled. The humidity measurement device is characterized in that the processor of diagnosis includes a determination part of diagnosis-start for determining whether the self-diagnosis can be started or not, based on an exchange state of the circumstances, and the gas temperature and the gas humidity before the heating control of circumstances gas, and a determination part of diagnosis-continuation for determining whether the self-diagnosis can be continued or not during the self-diagnosis, based on the gas temperature and the gas humidity that have been heating-controlled.

Advantageous Effects of Invention

According to the present invention, even in a state where contaminants adhere to a measurement element of humidity, or in a state where the measurement element of humidity is deteriorated, a highly reliable self-diagnosis technique can be provided. It should be noted that, problems, configurations, and effects other than those described above will be apparent from the following description of embodiments.

BRIEF DESCRIPTION OF DRAWINGS

FIG. 1 is a schematic view of a casing of relative humidity measurement device including an air intake system, according to Example 1 of the present invention.

DESCRIPTION OF EMBODIMENTS

Example 1

Figure 2A:
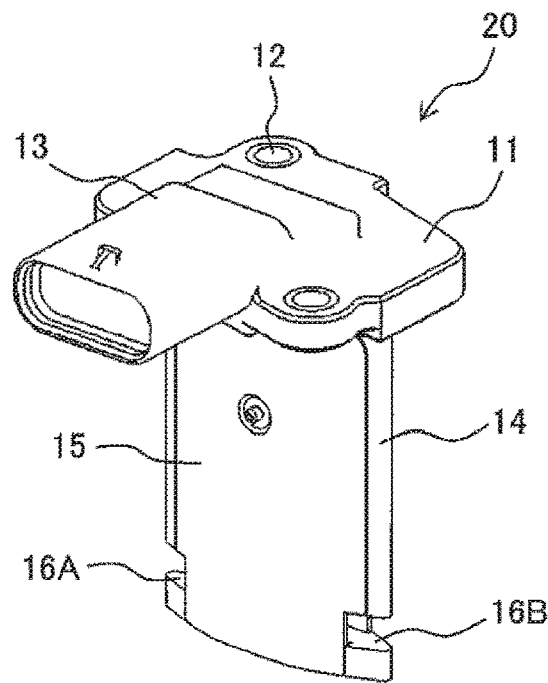
FIGS. 2A and 2B are schematic views of the casing of relative humidity measurement device according to Example 1 of the present invention.
Figure 2B:
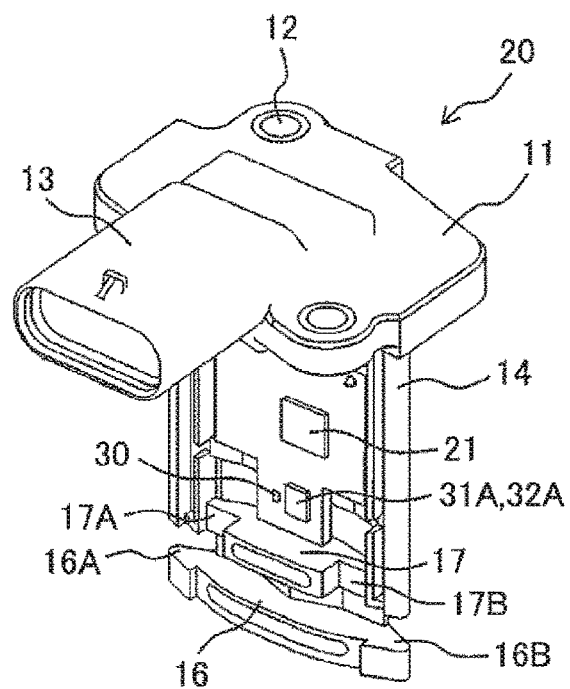
Figure 3:
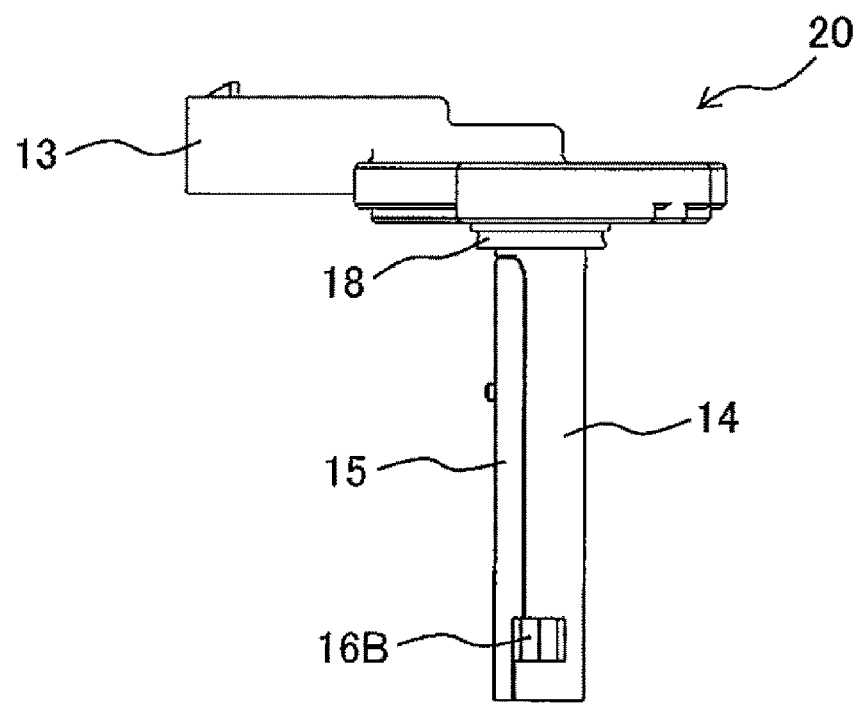
FIG. 3 is a side view of the casing of relative humidity measurement device according to Example 1 of the present invention.

Example 1 according to the present invention is described hereinafter with reference to FIGS. 1 through 10.

As illustrated in FIGS. 1, 2(a), 2(b), and 3, a humidity measurement device 20 according to Example 1 includes a supporting part of housing 11, a screw hole 12, a connector 13, a housing 14, a cover 15, a main passage 16 for taking a part of inlet air flowing in an air intake system 1, a sub passage 17 formed by the housing 14 and the cover 15, a heater element 30, a measurement element of temperature 31A, a measurement element of relative humidity 32A, and a control element of humidity measurement device 21.

The humidity measurement device 20 is inserted from an insertion hole provided on the wall of air intake system. 2 such that the main passage 16 can take a part of inlet air flowing in the air intake system 1. A humidity detection device 20 is fixed to a base 3, via the supporting part of housing 11, by a screw inserted into the screw hole 12. A gap generated when the humidity detection device 20 is fixed to the base 3 is filled with an O-ring 18.

The measurement element of relative humidity 32A is configured to be provided in the sub passage 17 branched from the main passage 16. Since most of contaminants taken into the main passage 16 move straight due to an inertial force, entry of the contaminants into the sub passage 17 can be prevented. Therefore, it is possible to prevent deterioration of the measurement element of relative humidity 32A due to adhesion of contaminants, by providing the measurement element of relative humidity 32A in the sub passage 17.

Figure 4:
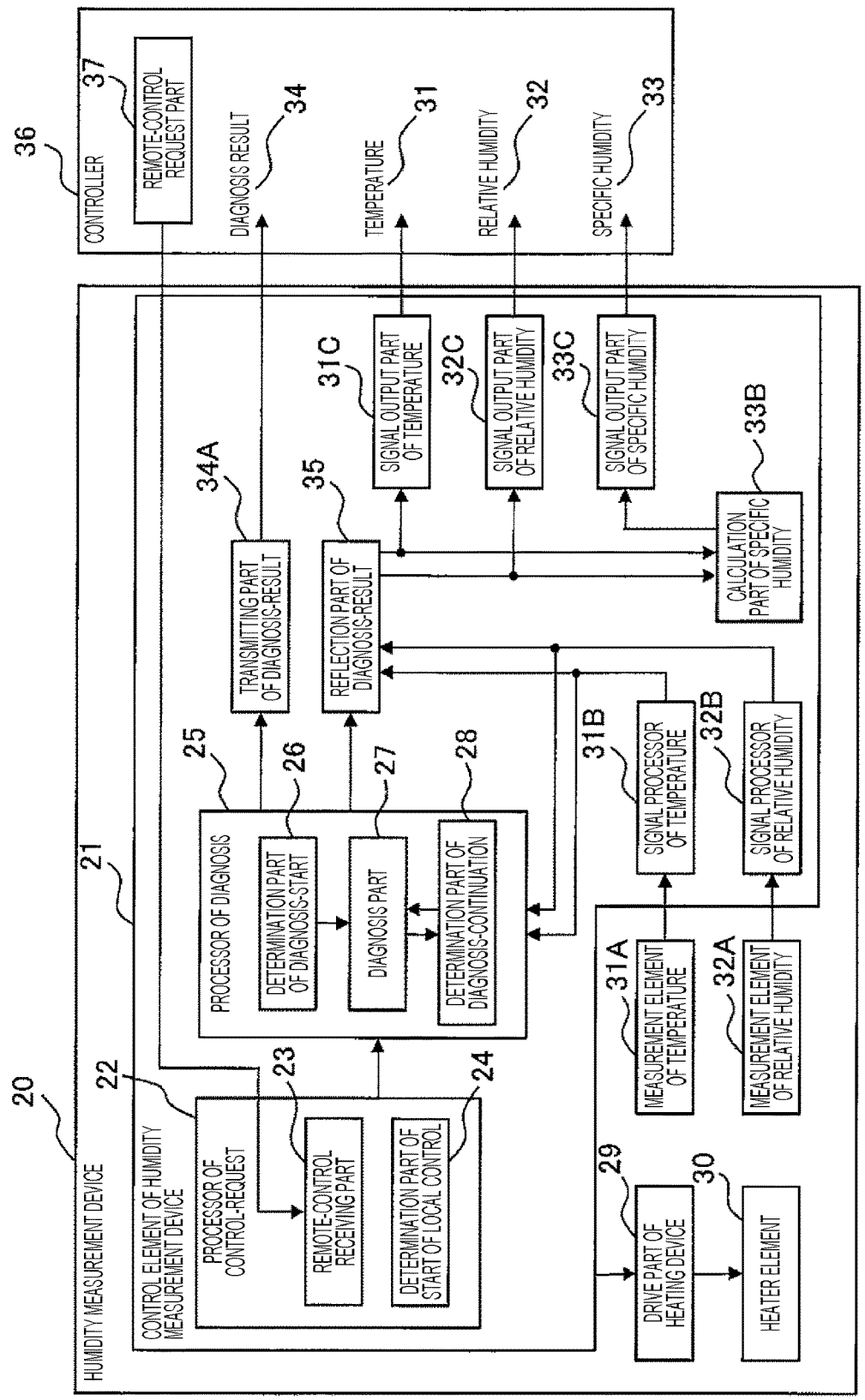
FIG. 4 is a block diagram showing a configuration according to Example 1 of the present invention.

As shown in FIG. 4, the humidity measurement device 20 includes the control element of humidity measurement device 21, a drive part of heating device 29, the heater element 30, the measurement element of temperature 31A, and the measurement element of relative humidity 32A.

The control element of humidity measurement device 21 includes a processor of control request 22, a processor of diagnosis 25, a signal processor of temperature 31B, a signal processor of relative humidity 32B, a calculation part of specific humidity 33B, a signal output part of temperature 31C, a signal output part of relative humidity 32C, a signal output part of specific humidity 33C, a transmitting part of diagnosis-result 34A, and a reflection part of diagnosis-result 35.

The processor of control request 22 includes a remote-control receiving part 23 for receiving a diagnosis request from a device other than the humidity measurement device 20 (hereinafter referred to as a remote-control request), for example a controller 36 or the like, and includes a determination part of start of local control 24. The processor of diagnosis 25 includes a determination part of diagnosis-start 26, a diagnosis part 27, and a determination part of diagnosis-continuation 28. The controller 36 includes a remote-control request part 37.

The humidity measurement device 20 receives and processes an output from the measurement element of temperature 31A with the signal processor of temperature 31B, then performs correction calculation with the reflection part of diagnosis-result 35, outputs a corresponding temperature 31 to the controller 36 with the signal output part of temperature 31C, receives and processes an output from the measurement element of relative humidity 32A with the signal processor of relative humidity 32B, then performs correction calculation with the reflection part of diagnosis-result 35, and then outputs a corresponding relative humidity 32 to the controller 36 with the signal output part of relative humidity 32C. Moreover, by using the output from the signal processor of temperature 31B, which has been corrected by the reflection part of diagnosis-result 35, and by using the output from the signal processor of relative humidity 32B, which has been corrected by the reflection part of diagnosis-result 35, the calculation part of specific humidity 33B is activated, and the signal output part of specific humidity 33C outputs a corresponding specific humidity 33 to the controller 36.

Figure 5:
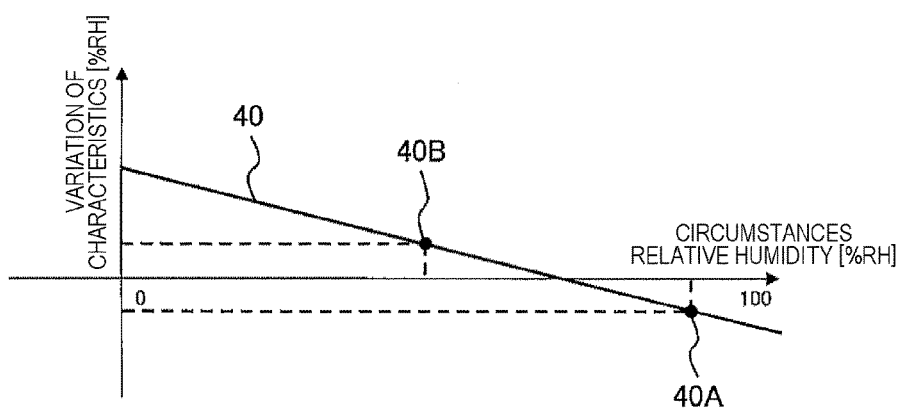
FIG. 5 is an explanation chart describing a correction amount of relative humidity according to Example 1 of the present invention.
Figure 6:
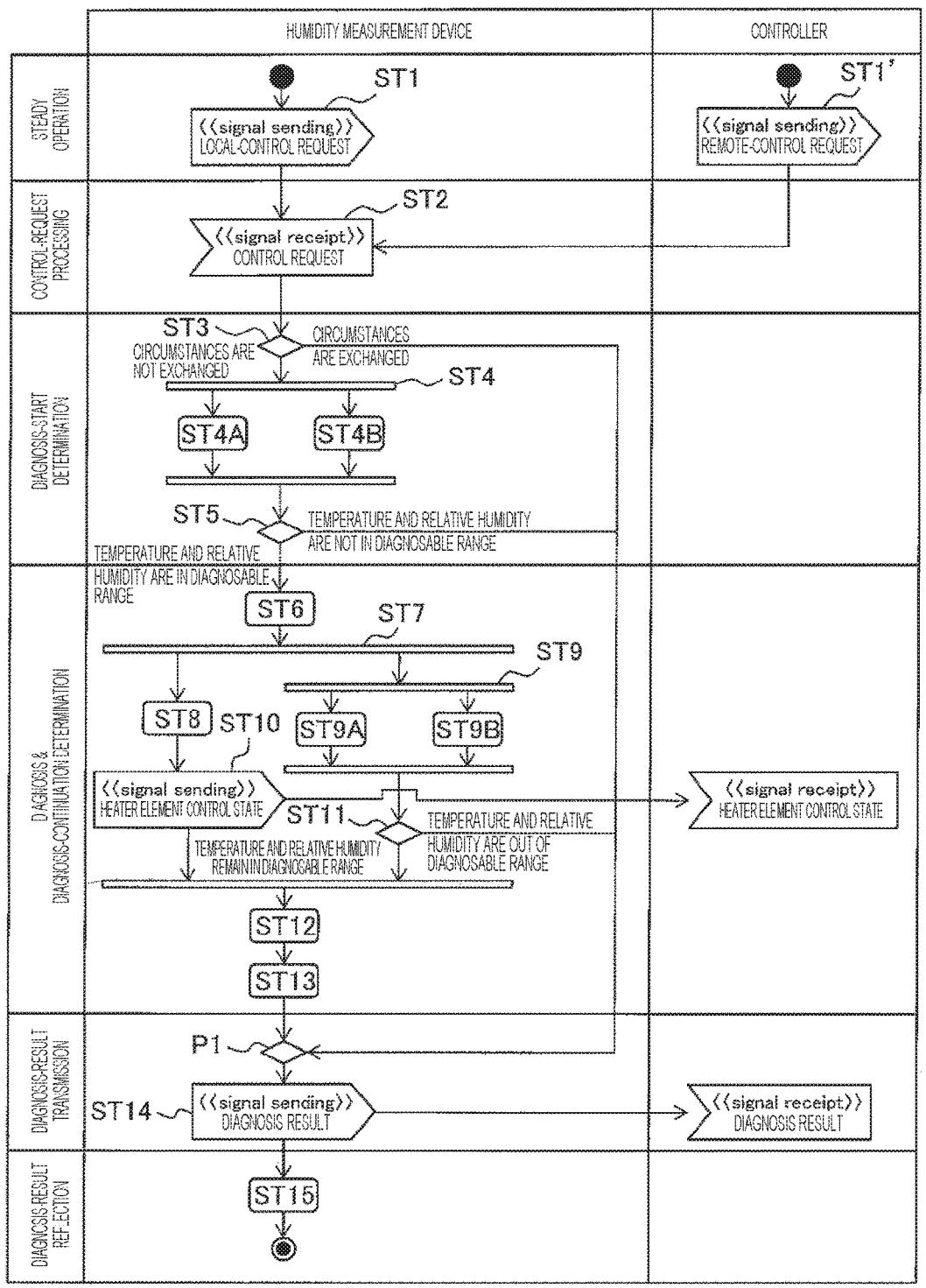
FIG. 6 is an activity diagram showing diagnosis processing and correction processing of output according to Example 1 of the present invention.
Figure 7:
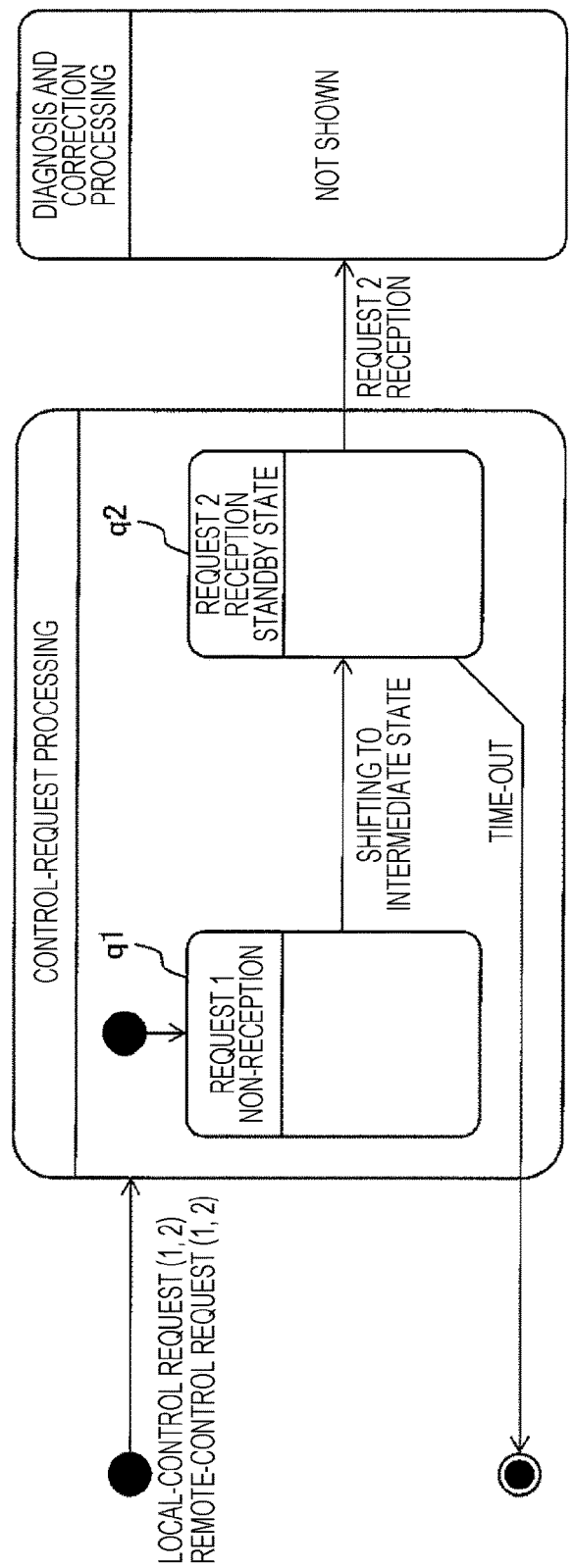
FIG. 7 is a state machine diagram when performing the diagnosis processing and the correction processing of output according to Example 1 of the present invention.
Figure 8:
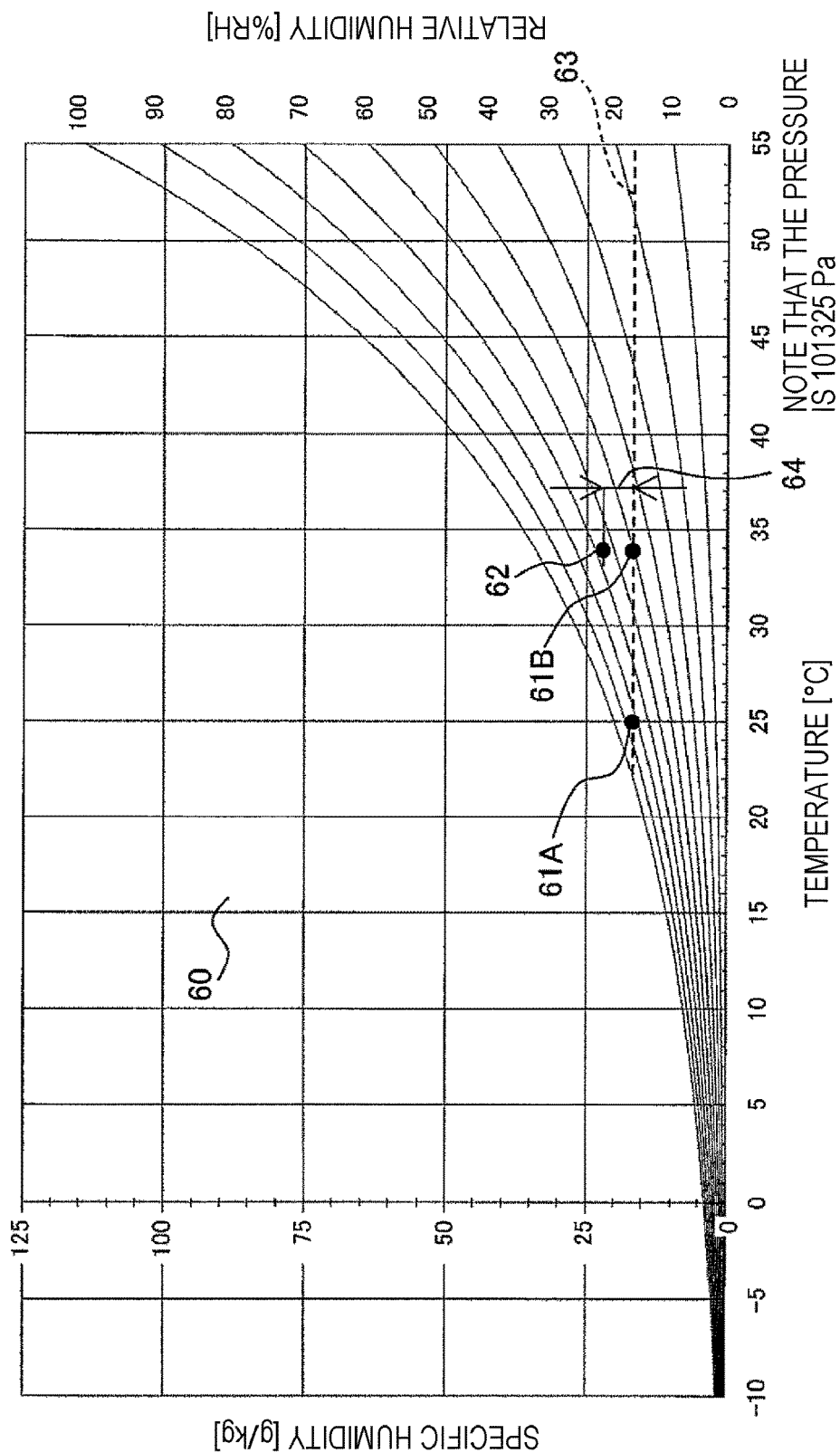
FIG. 8 is an explanation chart describing a range of diagnosable temperature/humidity according to Example 1 of the present invention.

Variation of output characteristics of the measurement element of relative humidity due to adhesion of contaminants or deterioration is described with reference to FIG. 5. In FIG. 5, a vertical axis indicates variation of characteristics, and a horizontal axis indicates a circumstances relative humidity (hereinafter referred to as a reference relative humidity). When variation of output characteristics of the relative humidity occurs due to adhesion of contaminants to the measurement element of relative humidity 32A, or due to aging deterioration of the measurement element of relative humidity 32A, a measurement error occurs for a reference relative humidity in the measurement element of relative humidity 32A. For example, the output characteristics change to output characteristics in variation of characteristics 40, such as taking a 1st measurement point 40A having minus variation of characteristics, or a 2nd measurement point 40B having plus variation of characteristics. Although there is described below a diagnostic method adopting a control method for improving reliability when a diagnosis is performed, the described diagnostic logic is one example, and can be applied to various diagnostic methods that change a relative humidity by changing temperature.

A method of self-diagnosis with improved reliability in Example 1 is described with reference to FIGS. 6, 7, 8, 9, and 10. A self-diagnosis and a reflection of a correction result are achieved by performing a steady operation process, a control-request processing process, a diagnosis-start determination process, a diagnosis & diagnosis-continuation determination process, a diagnosis-result transmission process, and a diagnosis-result reflection process.

Firstly, at a local-control request ST1 or a remote-control request ST1' in the steady operation process, the humidity measurement device 20 is requested to execute a diagnosis. Here, the local-control request ST1 and the remote-control request ST1' can be executed at any timing.

In the control-request processing process, a control request receiving part ST2 receives the local-control request ST1 or the remote-control request ST1', with which as a trigger, an internal condition shifts from a request 1 non-reception state q1 to a request 2 reception standby state q2, and then in the request 2 reception standby state q2, only when the local-control request ST1 or the remote-control request ST1' is received again, the internal condition shifts to a request reception state to execute diagnosis and correction processing of a post-stage. A time-out period is provided in the request 2 reception standby state q2, and if there is no other second request within a predetermined period after the shift to the request 2 reception standby state q2, the first request is rejected. It should be noted that the request 1 and the request 2 are not necessarily identical.

A circumstances exchange-state determination step ST3 in the diagnosis-start determination process determines whether circumstances gas is being exchanged or not. Here, a relationship among the specific humidity, the relative humidity, and the temperature generally becomes as shown in a moist air chart 60 in FIG. 8, which is obtained by Expression 1 below, and the determination is made according to whether the specific humidity is stable or not, since the specific humidity does not change when circumstances gas is not being exchanged.

$$SH = \frac{3801 \times RH \times \text{EXP}\left(\frac{17.62 \times \text{Temp}}{243.5 + \text{Temp}}\right)}{\text{Press} - 6.112 \times RH \times \text{EXP}\left(\frac{17.62 \times \text{Temp}}{243.5 \times \text{Temp}}\right)} \quad \text{[Expression 1]}$$

In Expression 1, SH is a circumstances specific humidity [g/kg], RH is a circumstances relative humidity [% RH], Temp is a circumstances temperature [° C.], and Press is a circumstances atmospheric pressure [Pa].

When it is determined that the circumstances gas is being exchanged in the circumstances exchange-state determination step ST3, and the following diagnosis processing is skipped to a merging-point of diagnosis-result transmission process P1 in the diagnosis-result transmission process. On the other hand, when it is determined that the circumstances gas is not being exchanged in the circumstances exchange-state determination step ST3, the processing proceeds to a temperature measurement and relative humidity measurement step ST4 (hereinafter referred to as a temperature/humidity measurement step 1 ST4).

Cases where it is determined that the circumstances gas is not being exchanged include, for example, a case where an engine is stopped, such as during idle reduction, at a time of key-less entry, or at a time of smart entry. Additionally, it is also possible to determine whether the circumstances gas is being exchanged or not, by measuring a flow rate of fluid flowing in the air intake system 1 with an air flow sensor or the like.

The temperature/humidity measurement step 1 ST4 performs in parallel a temperature measurement step ST4A for measuring a circumstances gas temperature with the measurement element of temperature 31A, and a relative humidity measurement step ST4B for measuring a circumstances gas relative humidity with the measurement element of relative humidity 32A.

A diagnosis-start determination step ST5 determines whether or not the temperature obtained at the temperature measurement step ST4A and the relative humidity obtained at the relative humidity measurement step ST4B are in a range of diagnosable temperature/humidity 50. It should be noted that, as shown in Expression 1, since the relative humidity can be obtained through a temperature and a specific humidity, the diagnosis-start determination step ST5 may determine whether the self-diagnosis can be started or not, with a combination of the temperature obtained at the temperature measurement step ST4A and the specific humidity of the state. Moreover, as shown in Expression 2 below, since the relative humidity can be obtained through a temperature and a dew-point temperature, the diagnosis-start determination step ST5 may also determine whether the self-diagnosis can be started or not, with a combination of the temperature obtained at the temperature measurement step ST4A and the dew-point temperature in the state.

$$E(t) = 6.11 \times 10^{\frac{a \times t}{t+b}} \quad \text{[Expression 2]}$$

$$RH = \frac{E(t)}{E(dp)} \times 100$$

$$\begin{cases} a = 7.5, b = 237.3 \ldots \text{ in a case of water} \\ a = 9.5, b = 265.5 \ldots \text{ in a case of ice} \end{cases}$$

In Expression 2, E is a circumstances saturated water vapor pressure [hPa], t is a circumstances temperature [° C.], RH is a circumstances relative humidity [% RH], dp is a circumstances dew-point temperature [° C.], and Press is a circumstances atmospheric pressure [Pa].

Figure 9:
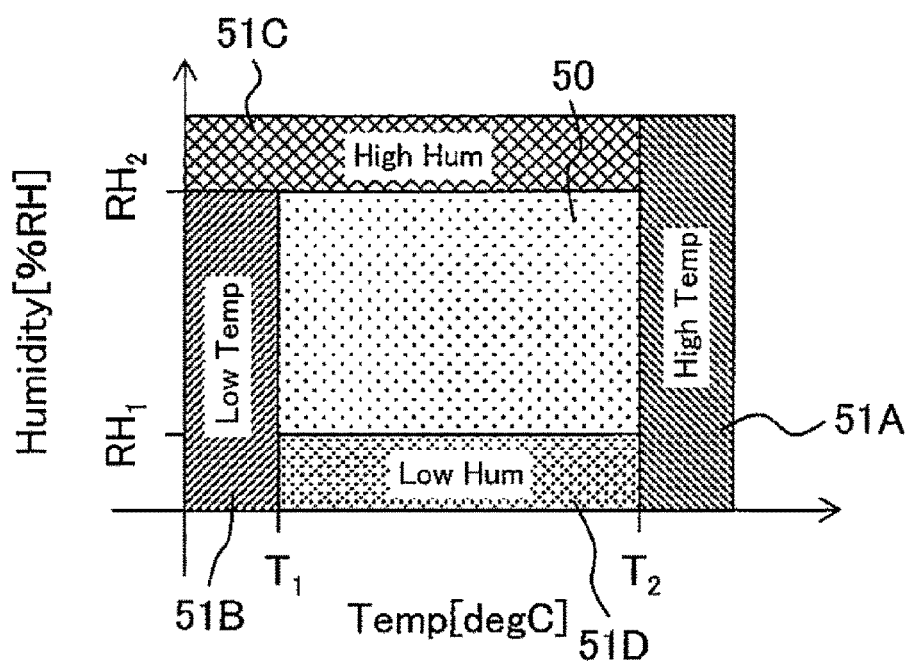
FIG. 9 is an explanation chart describing processing of diagnosis of characteristics and the correction amount of relative humidity according to Example 1 of the present invention.
Figure 10:
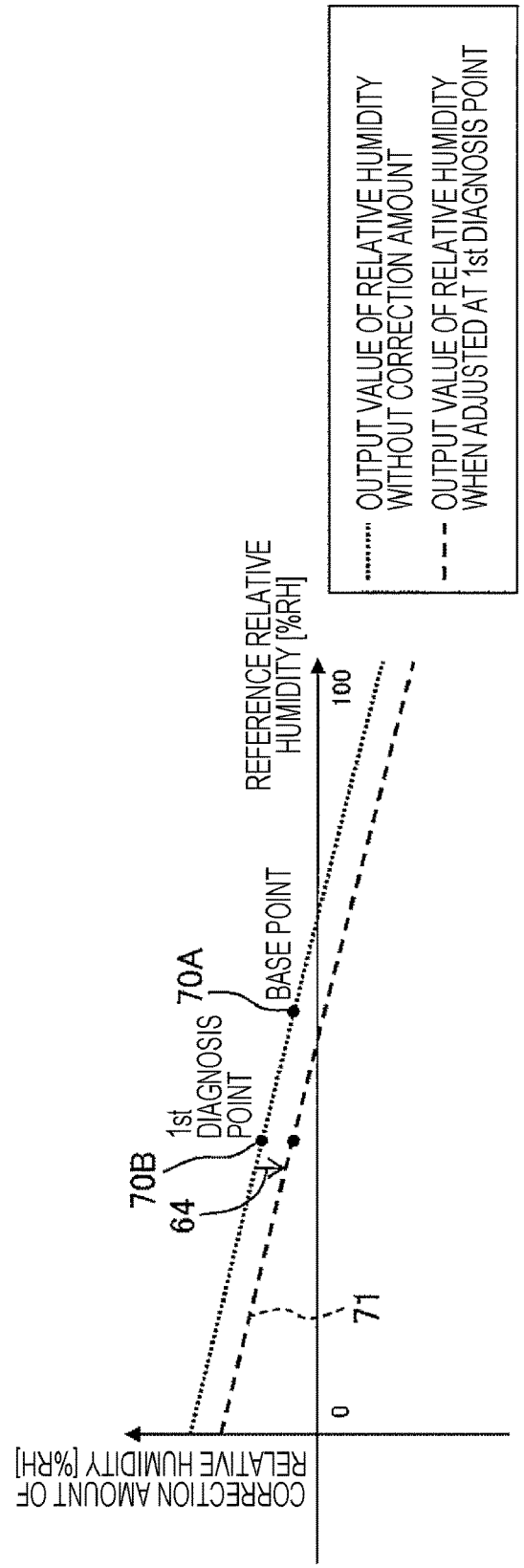
FIG. 10 is an explanation chart describing a relative humidity correction method according to Example 1 of the present invention.

Here, in FIG. 9, $T_1$ is a dew-point temperature [° C.] in circumstances, $T_2$ is a temperature value [° C.] obtained by subtracting a heat value generated in the heater element and peripheral circuits, from a junction temperature of the measurement element of relative humidity 32A or any element in the humidity measurement device 20, $RH_1$ is a humidity value (low-humidity side) [% RH] that can be accurately measured by the measurement element of relative humidity 32A, and $RH_2$ is a humidity value (high-humidity side) [% RH] that can be accurately measured by the measurement element of relative humidity 32A.

For example, there is a risk that a circumstances gas temperature may exceed the junction temperature of the element when further heating is performed while the circumstances gas temperature is in a high-temperature region 51A. Additionally, there is a risk that dew condensation is generated when heating is stopped while the circumstances gas temperature is in a low-temperature region 51B, or when heating is stopped while a circumstances gas humidity is in a high-humidity region 51C. Further, there is a risk that, when the circumstances gas humidity is in a low-humidity region 51D, a humidity change between before and after heating control is small, which prevents generation of a significant difference in a humidity condition, and thus degrades an accuracy.

Therefore, at the diagnosis-start determination step ST5, when it is determined that the circumstances temperature and relative humidity are not in the range of diagnosable temperature/humidity 50 (out of the range of diagnosable temperature/humidity), it is considered that the diagnosis cannot be started, and the following diagnosis processing is skipped to the merging-point of diagnosis-result transmission process P1 in the diagnosis-result transmission process. On the other hand, at the diagnosis-start determination step ST5, when it is determined that the circumstances temperature and relative humidity are in the range of diagnosable temperature/humidity 50, it is considered that the diagnosis can be started, and the processing proceeds to and after a specific-humidity calculation step ST6.

The specific-humidity calculation step ST6 in the diagnosis & diagnosis-continuation determination process calculates the specific humidity by applying the temperature obtained at the temperature measurement step ST4A and the relative humidity obtained at the relative humidity measurement step ST4B, to Expression 1. In this case, Press is one atmospheric pressure (101325 [Pa]).

A data-acquiring step ST7 in the diagnosis & diagnosis-continuation determination process performs in parallel a temperature control step ST8 for controlling a circumstances gas temperature by controlling a heating temperature of the heater element 30, and a temperature measurement and relative humidity measurement step ST9 (hereinafter referred to as a temperature/humidity measurement step 2 ST9). After the temperature control step ST8, or in parallel (not shown) with the temperature control step, via communication between the humidity measurement device 20 and the controller 36, for example, using a communication system such as LIN, CAN, SENT, FlexRay, or Ethernet (registered trademark), a signal is transmitted to the controller 36, in which the signal corresponds to each of states where the heater element 30 is controlled in an ON state by the control element of humidity measurement device 21, where the heater element 30 is controlled in an OFF state by the control element of humidity measurement device 21, where the heater element 30 is controlled in the ON state by the controller 36, and where the heater element is controlled in the OFF state by the controller 36. Accordingly, a state of heating control and information about which of the local-control request ST1 and the remote-control request ST1' has caused the diagnosis processing by the processor of diagnosis 25, are outputted (output part) to the controller 36, which is an external device.

The temperature/humidity measurement step 2 ST9 performs in parallel a temperature measurement step 2 ST9A for measuring a circumstances gas temperature with the measurement element of temperature 31A, and a relative humidity measurement step 2 ST9B for measuring a circumstances gas relative humidity with the measurement element of relative humidity 32A.

A diagnosis-continuation determination step ST11 in the diagnosis & diagnosis-continuation determination process determines whether the temperature obtained at the temperature measurement step 2 ST9A, and the relative humidity obtained at the relative humidity measurement step 2 ST9B, in the temperature/humidity measurement step 2 ST9, are in the range of diagnosable temperature/humidity 50. Here, when the relative humidity is not in the range of diagnosable temperature/humidity 50, there is a risk in each of the temperature regions 51A to 51D. Therefore, when it is determined that the relative humidity is not in the range of diagnosable temperature/humidity 50, it is considered that the diagnosis cannot be continued, the following processing is skipped to the merging-point of diagnosis-result transmission process P1 in the diagnosis-result transmission process. On the other hand, when it is determined that the relative humidity is in the range of diagnosable temperature/humidity 50, it is considered that the diagnosis can be continued, and the processing proceeds to a relative-humidity estimate-value calculation step ST12. It should be noted that, in the data-acquiring step ST7, execution may be repeated for different circumstances gas temperatures caused by the temperature control step ST8.

Here, modification of Expression 1 can provide Expression 3 below for calculating a relative humidity. When a state before the temperature control step ST8 (state before the heating control of the circumstances gas) is a condition A, and a state during the temperature control step ST8 (state where the circumstances gas is heating-controlled) is a condition B, Expression 4 below for estimating the relative humidity at the condition B can be obtained.

$$RH = \frac{\text{Press} \times SH}{(3801 + 6.112 \times SH) \times \text{EXP}\left(\frac{17.62 \times \text{Temp}}{243.5 + \text{Temp}}\right)} \quad \text{[Expression 3]}$$

$$RH_{Bestimate} = \frac{\text{Press} \times SH}{(3801 + 6.112 \times SH) \times \text{EXP}\left(\frac{17.62 \times (\text{Temp}_A + \Delta\text{Temp})}{243.5 + (\text{Temp}_A + \Delta\text{Temp})}\right)} \quad \text{[Expression 4]}$$

In Expression 4, $RH_{Bestimate}$ is a circumstances relative humidity [% RH] at the condition B, $\text{Temp}_A$ is a circumstances temperature [° C.] at the condition A, and $\Delta\text{Temp}$ is a temperature difference [° C.] between $\text{Temp}_A$ and a circumstances temperature at the condition B.

The relative-humidity estimate-value calculation step ST12 calculates an estimate value of relative humidity at the condition B by applying the specific humidity at the condition A, which is obtained at the specific-humidity calculation step ST6, and the temperature at the condition B, which is obtained at the temperature measurement step 2 ST9A, to Expression 4. This utilizes that, when the circumstances gas is not in the exchange state, the specific humidity does not change between the condition A and the condition B, and thereby follows an ideal output characteristics of relative humidity 63 (see FIG. 8). In this case, similarly to the specific-humidity calculation step ST6, Press is one atmospheric pressure (101325 [Pa]). Namely, the relative-humidity estimate-value calculation step ST12 calculates an estimate value of the relative humidity 61B at the condition B from a measurement value of relative humidity 61A at the condition A.

A relative-humidity-difference calculation step ST13 in the diagnosis & diagnosis-continuation determination process compares the estimate value of the relative humidity 61B at the condition B, which is calculated at the relative-humidity estimate-value calculation step ST12, and a measurement value 62 of the relative humidity at the condition B, which is actually measured at the relative humidity measurement step ST9B, and calculates variation of characteristics 64 at the condition B from a difference between the measurement value and the estimate value.

The merging-point of diagnosis-result transmission process P1 in the diagnosis-result transmission process is shifted from the circumstances exchange-state determination step ST3, the diagnosis-continuation determination step ST11, and the relative-humidity-difference calculation step ST13, and proceeds to a diagnosis-result transmission step ST14.

In the diagnosis-result transmission step ST14, via communication between the humidity measurement device 20 and the controller 36, for example, using a communication system such as LIN, CAN, SENT, FlexRay, or Ethernet (registered trademark), a result of the diagnosis is transmitted to the controller 36. For example, when the merging-point of diagnosis-result transmission process P1 is shifted from the circumstances exchange-state determination step ST3, it is considered that the self-diagnosis cannot be started, and a signal is transmitted, corresponding to that the circumstances are exchanged and thereby the diagnosis is canceled. Further, when the merging-point of diagnosis-result transmission process P1 is shifted from the diagnosis-continuation determination step ST11, it is considered that the diagnosis cannot be continued, and a signal is transmitted, corresponding to each of cases where the temperature obtained at the temperature measurement step 2 ST9A in the temperature/humidity measurement step 2 ST9 is in the high-temperature region 51A, where the temperature is in the low-temperature region 51B, where the relative humidity obtained at the relative humidity measurement step 2 ST9B is in the high-humidity region 51C, and where the relative humidity is in the low-humidity region 51D.

The diagnosis-result reflection step ST15 in the diagnosis-result reflection process performs correction of the variation of characteristics 64 at the condition B, which is calculated at the relative-humidity-difference calculation step ST13, to the relative humidity at the condition B, and thereby can reduce a measurement error at the condition B. Alternatively, diagnosis-result reflection step ST15 performs an overall range correction of relative humidity to obtain an output characteristics of relative humidity 71 when adjusted at a 1st diagnosis point 70B, and thereby can reduce a measurement error at the condition B. Here, a base point 70A corresponds to a measurement point at the condition A, and the 1st diagnosis point 70B corresponds to a measurement point at the condition B (see FIG. 10).

In Example 1 according to the present invention, an intermediate state is interposed between the steady state and the diagnostic state, which makes possible to avoid, for example, an unexpected diagnosis due to noise, and to prevent an abnormal diagnosis-result due to an invalid diagnosis, and degradation of a measurement accuracy of a measured value of relative humidity.

Further, by measuring the temperature and the relative humidity to determine diagnosis propriety before performing the diagnosis, it is possible to avoid a risk that the junction temperature is exceeded due to further heating while the circumstances are at a high temperature, a risk that dew condensation is generated due to stop of heating while the circumstances are at a low temperature, a risk that dew condensation is generated due to stop of heating while the circumstances are high in humidity, and a risk that, when the circumstances are low in humidity, generation of a significant difference between states before and after temperature control is prevented, causing degradation of an accuracy. Thus it is possible to response to a diagnosis request from the external controller 36, which cannot recognize a state of the humidity measurement device 20.

Furthermore, notifying the external controller 36 of a state of the heater element during execution of the diagnosis processing allows identification of a change factor of a measured value of temperature/humidity, and notifying the external controller 36 of a diagnosis result allows prevention of an unnecessary control of the external controller 36.

Therefore, according to Example 1 of the present invention, the highly reliable humidity measurement device 20 can be provided when the diagnosis is started by the local-control request from the humidity measurement device 20 itself, and when the diagnosis is started by the remote-control request from the controller 36 external of the humidity measurement device 20, in a state where contaminants adhere to the measurement element of relative humidity 32A, or a state where the measurement element of relative humidity 32A is deteriorated.

Example 2

Figure 11:
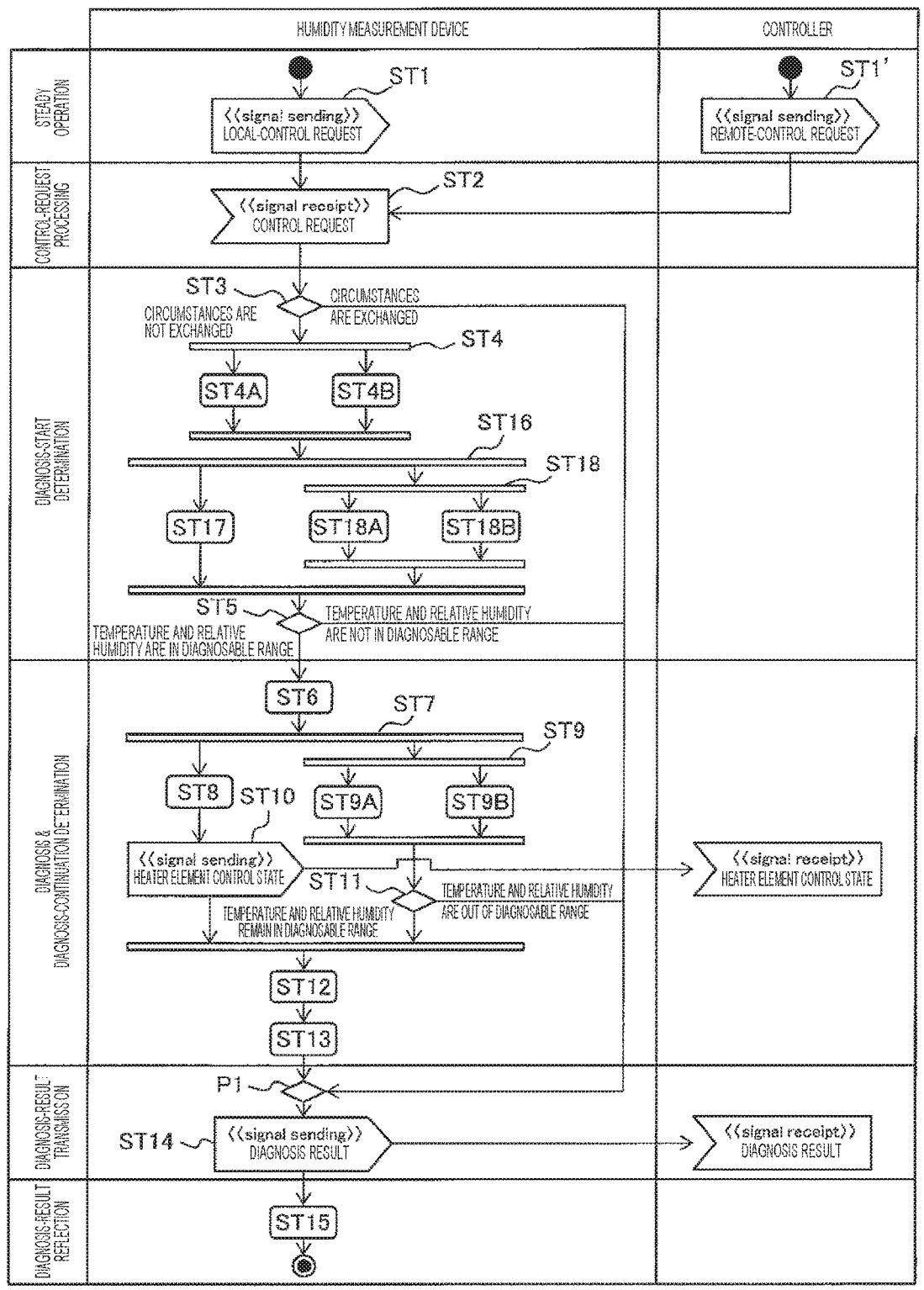
FIG. 11 is an activity diagram showing diagnosis processing and correction processing of output according to Example 2 of the present invention.

Example 2 according to the present invention is described hereinafter with reference to FIG. 11. It should be noted that same configurations as Example 1 are omitted.

In Example 2, a temperature/humidity adjustment step ST16 is added after a temperature/humidity measurement step 1 ST4. The temperature/humidity adjustment step ST16 performs in parallel a temperature control step 2 ST17 and a temperature control step 3 ST18 for controlling a circumstances gas temperature.

The temperature control step 3 ST18 performs in parallel a temperature measurement step 3 ST18A for measuring a circumstances gas temperature with the measurement element of temperature 31A, and a relative humidity measurement step 3 ST18B for measuring a circumstances gas relative humidity with the measurement element of relative humidity 32A.

The temperature/humidity adjustment step ST16 includes processing for previously adjusting temperature and relative humidity in a range of diagnosable temperature/humidity 50, by stopping heating when a heater element 30 is heating in a high-temperature region 51A, by heating when the heater element 30 is not heating in a low-temperature region 51B, by heating when the heater element 30 is not heating in a high-humidity region 51C, and by stopping heating when the heater element 30 is heating in a low-humidity region 51D, in the range of diagnosable temperature/humidity 50.

It should be noted that the process that executes processing for previously making the temperature/humidity in a condition suitable for the diagnosis is not only in the diagnosis-start determination process, for example, it can be executed in various processes such as a steady operation, other than during the diagnosis.

According to Example 2 of the present invention, by previously controlling a gas temperature and a gas humidity that are detected by the humidity measurement device 20 to a value suitable for the diagnosis, it is possible to immediately response to a diagnosis request from an external controller 36, and to reduce a processing time. Therefore, opportunities for a diagnosis can be increased in limited time where the circumstances gas is not exchanged, such as during idle reduction, at a time of key-less entry, or at a time of smart entry.

Example 3

Example 3 according to the present invention is described hereinafter with reference to FIGS. 12(a) and 12(b). It should be noted that same configurations as Examples 1 and 2 are omitted.

Figure 12A:
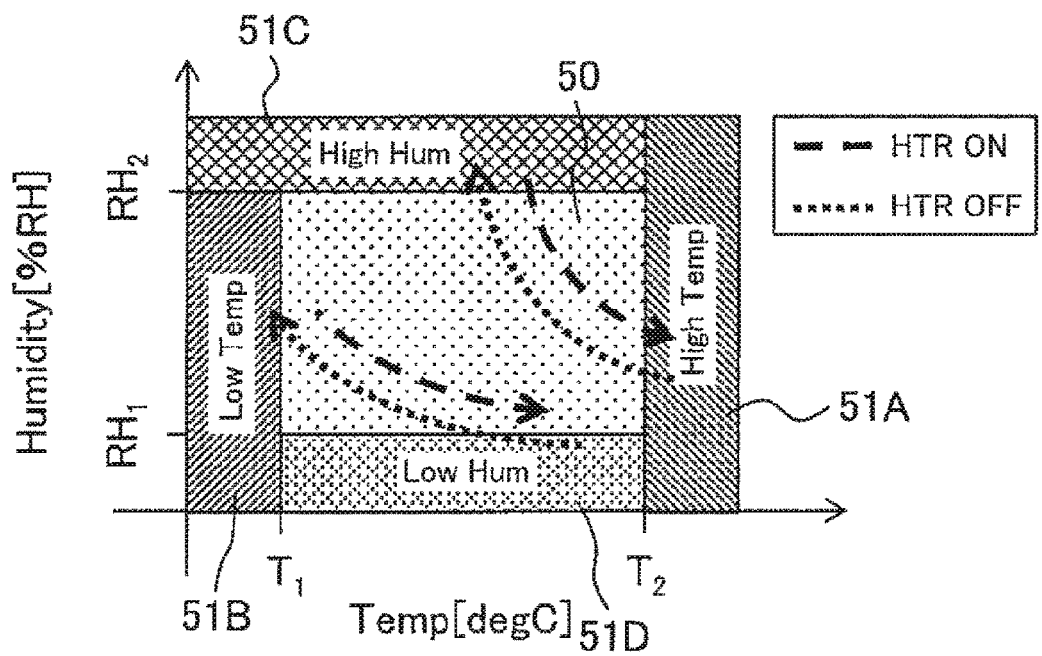
FIGS. 12A and 12B are explanation charts describing processing of diagnosis of characteristics and a correction amount of relative humidity according to Example 3 of the present invention.
Figure 12B:
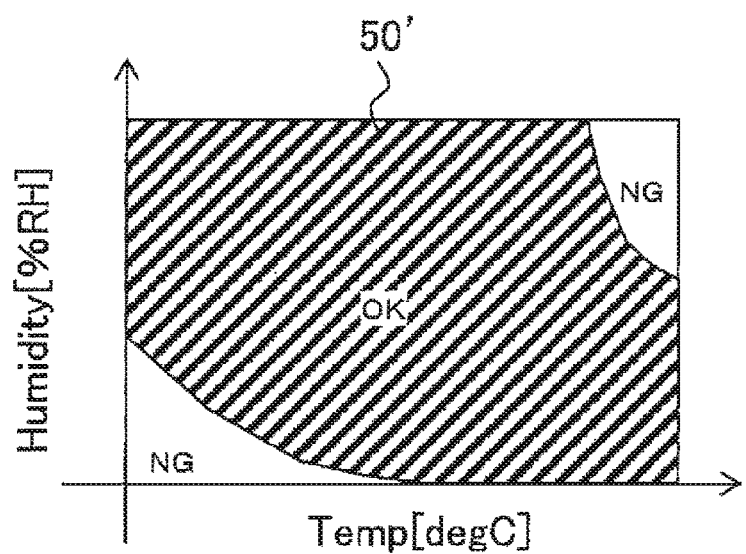

In Example 3, a range of diagnosable temperature/humidity (OK range) is expanded to a region 50' (range of diagnosable temperature/humidity 50') shown in FIG. 12(b), which is a larger region than a region 50 shown in FIG. 12(a).

For example, when a diagnosis-start determination step ST5 and a diagnosis-continuation determination step ST11 are performed, there are cases where diagnosis can be performed by stopping heating when a heater element 30 is heating in a high-temperature region 51A, by heating when the heater element 30 is not heating in a high-humidity region 51C, and by stopping heating when the heater element 30 is heating in a low-humidity region 51D. Therefore, the range of diagnosable temperature/humidity (OK range) can be expanded to the region 50' shown in FIG. 12(b), which is the larger region than the region 50 shown in FIG. 12(a).

According to Example 3 of the present invention, by providing the larger range of diagnosable temperature/humidity (OK range) that is used at the diagnosis-start determination step ST5 and the diagnosis-continuation determination step ST11, diagnosable opportunities can be increased.

Although embodiments of the present invention have been described in detail above, the invention is not limited to the above embodiments, and various modifications of design may be made without departing from the spirit of the invention described in claims. For example, the above embodiments have been illustrated in detail to facilitate description for easy understanding, and are not necessarily limited to the examples that include all the illustrated configurations. Moreover, a part of a configuration of an embodiment can be replaced with a configuration of another embodiment, and a configuration of an embodiment can also be added with a configuration of another embodiment. Moreover, part of a configuration of each embodiment may be deleted, replaced, added with another configuration.

REFERENCE SIGNS LIST 20 humidity measurement device
21 control element of humidity measurement device
22 processor of control-request
23 remote-control receiving part
24 determination part of start of local control
25 processor of diagnosis
26 determination part of diagnosis-start
27 diagnosis part
28 determination part of diagnosis-continuation
29 drive part of heating device
30 heater element
31 temperature
31A measurement element of temperature
31B signal processor of temperature
31C signal output part of temperature
32 relative humidity
32A measurement element of relative humidity
32B signal processor of relative humidity
32C signal output part of relative humidity
33 specific humidity
33B calculation part of specific humidity
33C signal output part of specific humidity
34 diagnosis result
34A transmitting part of diagnosis-result
35 reflection part of diagnosis-result
36 controller
37 remote-control request part
40 output characteristics in variation of characteristics
40A 1st measurement point
40B 2nd measurement point
50 range of diagnosable temperature/humidity
50' range of diagnosable temperature/humidity
51A high-temperature region
51B low-temperature region
51C high-humidity region
51D low-humidity region
60 moist air chart

The invention claimed is:

1. A humidity measurement device comprising:
a temperature measurement element;
a humidity measurement element;
a diagnostic processor that performs a self-diagnosis by using a gas temperature and a gas humidity measured by the temperature measurement element and the humidity measurement element, respectively, before heating control of a gas in a measurement environment, and a gas temperature and a gas humidity of the gas that have been heating-controlled, wherein
the diagnostic processor comprises
a diagnosis-start determination part for determining whether the self-diagnosis can be started or not, based on an exchange state of the measurement environment, and the gas temperature and the gas humidity of the gas before heating control of the gas, and
a diagnosis-continuation determination part for determining whether the self-diagnosis can be continued or not, during the self-diagnosis, based on the gas temperature and the gas humidity of the gas that have been heating-controlled, and
a diagnosis part, wherein, when the diagnosis-continuation determination part determines that the self-diagnosis can be continued, the diagnosis part calculates a specific humidity by using the gas temperature and the gas humidity of the gas before the heating control, calculates an estimate value of relative humidity by using the gas temperature that has been heating-controlled and the specific humidity, and calculates a variation of characteristics from a difference between the gas humidity measured after the heating control and the estimate value.

2. The humidity measurement device according to claim 1, wherein the humidity measurement device comprises a diagnosis-result reflection part for correcting the gas humidity that has been heating-controlled by adjusting a gas humidity output value by an amount of the variation of characteristics calculated by the diagnosis part.

3. The humidity measurement device according to claim 1, wherein
the diagnosis-start determination part determines that the self-diagnosis can be started when the gas temperature and the gas humidity before the heating control are in a predetermined range, and
the diagnosis-continuation determination part determines that the self-diagnosis can be continued when the gas temperature and the gas humidity that have been heating-controlled are in the predetermined range.

4. The humidity measurement device according to claim 1, wherein
the humidity measurement device comprises a control request processor for performing a control request of the self-diagnosis to the diagnostic processor based on an own local-control request or a remote-control request by another device, and
the diagnostic processor, by receiving a control request from the control request processor, performs determination processing for determining whether diagnosis can be started or not, with the diagnosis-start determination part.

5. The humidity measurement device according to claim 4, wherein the control request processor, by receiving the local-control request or the remote-control request, shifts an internal condition from a request non-reception state to a request reception standby state, and by receiving the local-control request or the remote-control request again within a predetermined period after the shift to the request reception standby state, shifts the internal condition from the request reception standby state to a request reception state to perform a control request of the self-diagnosis.

6. The humidity measurement device according to claim 5, wherein the humidity measurement device comprises an output part for outputting, to an external device, a state of the heating control and information about which of the local-control request and the remote-control request has caused the diagnosis processing by the diagnostic processor.

7. The humidity measurement device according to claim 1, wherein the humidity measurement device comprises a diagnosis-result transmitting part for outputting a diagnosis result to an external device when the diagnosis-start determination part determines that the self-diagnosis cannot be started, or when the diagnosis-continuation determination part determines that the self-diagnosis cannot be continued.

8. The humidity measurement device according to claim 1, wherein
the humidity measurement device comprises a heater element for heating the gas in the measurement environment, and
when the gas temperature and the gas humidity before the heating control are out of a predetermined range of diagnosable temperature/humidity, the diagnosis-start determination part controls the heater element to adjust the gas temperature and the gas humidity in the predetermined range of diagnosable temperature/humidity, and determines that the self-diagnosis can be started when the adjusted gas temperature and gas humidity are in the predetermined range of diagnosable temperature/humidity.

* * * * *